United States Patent [19]
Goel

[11] 3,946,015
[45] Mar. 23, 1976

[54] PROCESS FOR THE PREPARATION OF ACID CHLORIDES
[75] Inventor: Om P. Goel, Detroit, Mich.
[73] Assignee: Parke, Davis & Company, Detroit, Mich.
[22] Filed: July 11, 1974
[21] Appl. No.: 487,525

[52] U.S. Cl. 260/268 H; 260/247.2 A; 260/247.2 R; 260/293.69; 260/294.9; 260/295.5 R; 260/239.1; 260/243 C; 424/246; 424/248; 424/250; 424/263; 424/267
[51] Int. Cl.² .............. C07D 419/14; C07D 413/04; C07D 413/14; C07D 401/04
[58] Field of Search.... 260/295.5 R, 293.69, 268 H, 260/247.2 A

[56] References Cited
UNITED STATES PATENTS
3,503,986   3/1970   Seidel et al. ................. 260/295.5 R
3,576,814   4/1971   Seidel et al. ................. 260/295.5 R Primary Examiner—John D. Randolph
Assistant Examiner—Robert T. Bond

[57]     ABSTRACT

A process for the production of 6-(disubstituted amino)phenyl-1,2-dihydro-2-oxonicotinyl chloride hydrochlorides, which comprises exposing the dry, finely divided corresponding 6-(disubstituted amino)phenyl-1,2-dihydro-2-oxonicotinic acid or its hydrochloride to gaseous thionyl chloride utilizing reduced atmospheric pressures. The 6-(disubstituted amino)phenyl-1,2-dihydro-2-oxonicotinyl chloride hydrochlorides are useful as intermediates in the preparation of useful semisynthetic antibiotics.

4 Claims, 1 Drawing Figure

U.S. Patent   March 23, 1976   3,946,015
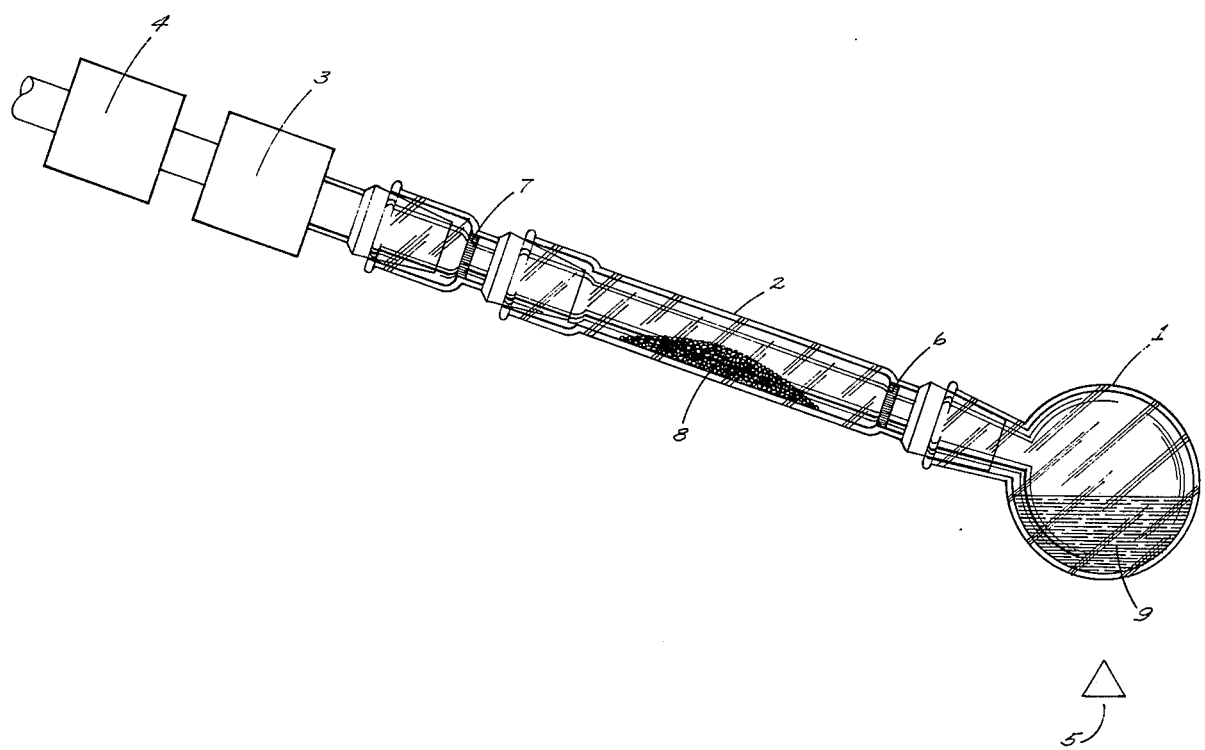

PROCESS FOR THE PREPARATION OF ACID CHLORIDES

SUMMARY AND DETAILED DESCRIPTION

The present invention relates to a process for the production of 6-(disubstituted amino)phenyl-1,2-dihydro-2-oxonicotinyl chloride hydrochlorides having the formula

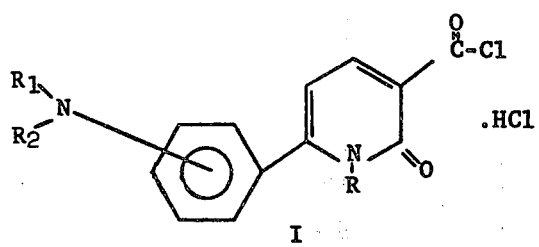

I wherein R is hydrogen or methyl; $R_1$ and $R_2$ are branched or straight chain lower alkyl groups of from one to six carbon atoms, or $R_1R_2N$ taken together is 4-$R_3$-1-piperazino, 4-methyl-1-homopiperazino, 1-pyrrolidino, morpholino, 1-piperidino, 4-(1-pyrrolidino)-piperidino or 4-(1-piperidino)-piperidino, wherein $R_3$ is a branched or straight chain lower alkyl group of from one to six carbon atoms, cyclohexyl, benzyl, phenyl, halophenyl wherein halo represents chloro, fluoro, bromo, or iodo; which comprises reacting a compound of the formula

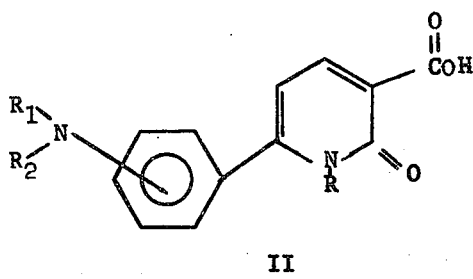

II wherein R, $R_1$ and $R_2$ are as previously defined or acid addition salts thereof with thionyl chloride wherein said thionyl chloride is in the gaseous phase.

The preferred embodiments of the process give rise to compounds wherein R is hydrogen; $R_1R_2N$ taken together is 4-$R_3$-1-piperazino and $R_3$ is a straight or branched lower alkyl group of from one to six carbon atoms or benzyl. The most preferred embodiments of this process are those wherein the $R_1R_2N$ group is in the para position.

Typical acid addition salts are the hydrochloride, hydrobromide, sulfate or phosphate salts, with the preferred salt being the hydrochloride salt.

In the past, the useful starting materials of this invention were generally prepared by reacting a compound of formula II, which exhibit a low order of solubility in most organic solvents, or an acid addition salt thereof, with thionyl chloride in the liquid state. Thus, a compound of formula II or its acid addition salt was usually suspended in an organic solvent and the thionyl chloride was added to said suspension. The resulting compound of formula I was removed by filtration under nitrogen and taken on directly to the next step in the preparation of useful antimicrobials. Unfortunately, the foregoing precedure possesses a number of drawbacks. The products of the general formula I are very finely divided, resulting in very slow rates of filtration and a significant tendency to clog the filters. In addition, large excesses of thionyl chloride must be employed in this procedure, thus requiring additional recovery steps.

The procedure of this invention, which utilizes gaseous thionyl chloride, removes the undesirable filtration under nitrogen step completely. In addition, lesser quantities of thionyl chloride are employed and the unreacted thionyl chloride is recovered by simply trapping the material. The advantages are self evident when comparing this process to the previous approach which requires costly and time consuming distillation recovery steps.

The 6-[(substituted amino)phenyl]-1,2-dihydro-2-oxonicotinic acid compounds and their reactive derivatives which are required as starting materials in the foregoing process can be prepared according to any of a variety of methods as illustrated in greater detail hereinafter.

A compound of the formula

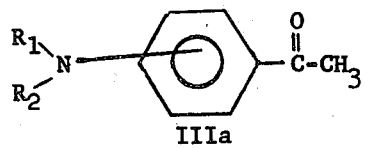

IIIa is prepared by alkylating a compound of the formula

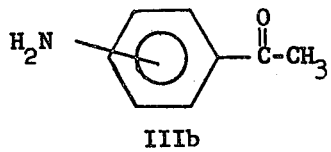

IIIb with an alkylating agent, such as an alkyl iodide or dialkyl sulfate; or reacting a compound of the formula

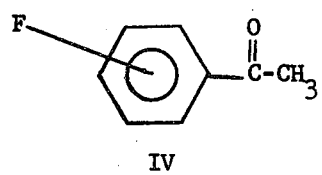

IV wherein the fluorine is in the ortho or para position, with an amine of the formula

In order to obtain meta disubstituted aminoacetophenones, the procedure shown in Compt. rend. 235, 546 (1952), which is incorporated by reference, may be employed.

The compound of the formula

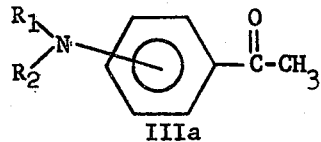

IIIa is reacted with a lower alkyl formate, such as ethyl formate, in the presence of a strong base, such as sodium methoxide or sodium hydride, to give the sodium salt of the following dicarbonyl compound

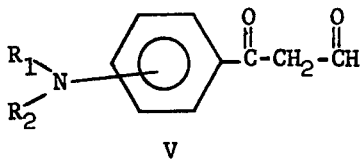

V

This compound in turn is reacted with 2-cyanoacetamide in the presence of piperidine acetate or a reagent which adjusts the pH to about 9 to give the following nitrile

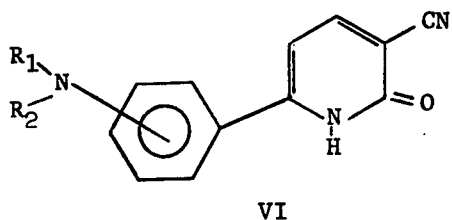

VI

The above nitrile may also be prepared by reacting a compound of the formula

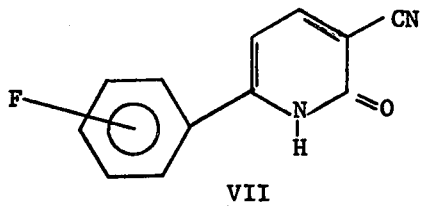

VII wherein the fluorine is in the ortho or para position, with a compound of the formula

If desired, the resulting nitrile may be methylated utilizing methyl iodide/possium hydroxide to give a compound of the formula

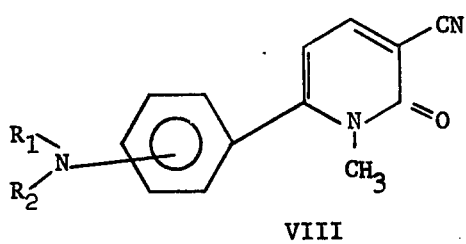

VIII

Compounds of the formula

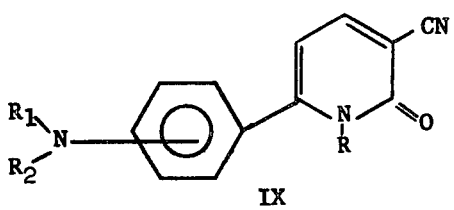

IX wherein R, $R_1$ and $R_2$ are as previously defined, which are prepared by the above procedures, are converted to the desired 6-[(substituted amino)phenyl]-1,2-dihydro-2-oxonicotinic acid by conversion of the cyano group to a carboxyl group utilizing an aqueous solution of a strong base. After neutralization of the free base, one obtains the free acid of formula II. The addition of excess acid gives rise to the acid addition salt of a compound of formula II. Typical acids that may be used for this purpose are hydrochloric acid, sulfuric acid, phosphoric acid, etc.

The compounds of the formula II and acid addition salts thereof are converted into compounds of the formula I by reaction with thionyl chloride in the gaseous phase. This is achieved by carrying out the reaction under slightly reduced pressure. The range of pressures employed are from about 0.1 atmospheres to about 0.5 atmospheres, preferably about 0.2 atmospheres.

The higher the temperature at which the thionyl chloride (which is to be vaporized to supply gaseous thionyl chloride) is maintained, the lesser the reduction of pressure required for carrying out the reaction. Generally, the thionyl chloride to be vaporized is maintained at a temperature of from about 20° to about 40°C., preferably about 28°C. While the reaction time is not critical, generally periods of from a few minutes to about 72 hours are utilized, preferably about 1 hour to 48 hours.

A compound of formula II, or an acid addition salt thereof, is generally employed utilizing material of an average particle size of less than 8 microns in diameter to give maximum exposure to the gaseous thionyl chloride.

In order to further ensure complete exposure to the thionyl chloride, it is preferred that the compound of formula II, or an acid addition salt thereof, be mixed during exposure to the gaseous thionyl chloride.

The invention can conveniently be carried out in the apparatus shown in the drawing, although various modifications and alterations of the apparatus will become apparent to those skilled in the art without departing from the scope and spirit of this invention. It should be understood that the process is not necessarily limited to one which need be carried out in the apparatus described in the drawing.

Referring now to the drawing, liquid thionyl chloride is placed in the distillation flask 1, which may optionally be heated by a source of heat 5. A compound of the formula II 8 is placed in the tube 2 which is connected to the flask 1 containing liquid thionyl chloride 9, which is preferably separated by a sintered glass disc 6 disposed in the neck of the latter. The tube 2 is preferably connected to the trap 3 which generally is a form of a condenser which will liquify gaseous thionyl chloride. Preferably, a second sintered glass disc 7 is disposed between the trap 3 and the tube 2. The trap 3, in turn, is connected to a means for creating a vacuum 4, such as a vacuum pump. Ideally, the cylindrical portion of the apparatus is mechanically rotated during the reaction to maximize the exposure of the compound of the formula II to the gaseous thionyl chloride.

The intermediates prepared according to the process of this invention, when reacted with ampicillin (X), cephalexin (XI), or cephaloglycin (XII) or the acid salt or silylated derivative thereof give rise to a compound of the following structure

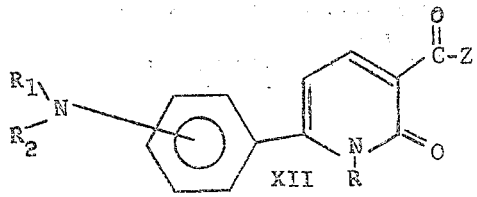

wherein R, $R_1$ and $R_2$ are as previously defined and Z is

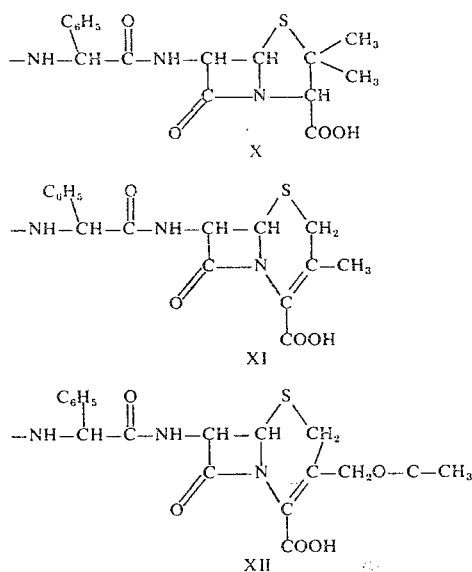

The above described products, and salts thereof, which are the subject matter of co-pending U.S. Pat. application No. 434,763, filed Jan. 21, 1974 which is incorporated by reference, are potent antimicrobial agents. More specifically, these compounds exhibit marked antimicrobial activity against *Klebsiella pneumoniae, Serratia marcescens, Enterobacter aerogenes* and *Pseudomonas aeruginosa*.

The invention is illustrated by the following example:

EXAMPLE:

An apparatus is constructed according to the drawing. Thus, a cylindrical tube (10 inch × ¾ inch) is packed with 8–10 Gm. of 1,2-dihydro-6-[p-(4-methyl-1-piperazinyl)-phenyl]-2-oxonicotinic acid, fitted with an adapter and placed on a distillation flask containing 80–100 ml. of thionyl chloride. This assembly is then fitted on to the rotating head of a conventional rotating evaporator at a slight downward angle and the thionyl chloride evaporated under a vacuum over 16-18 hours (the vacuum applied is adjusted by using a nitrogen bleed valve in the system so as to allow complete evaporation in 16-18 hours). The solid tumbles in the rotating tube and slowly changes from a green-yellow to bright orange color. After all the thionyl chloride has evaporated, the product can be dried free of excess thionyl chloride by leaving the system under vacuum for 2-3 hours. The product is then collected from the tube and taken on to the next reaction step. The thionyl chloride vapor is condensed and reused.

According to the above procedure, upon substituting in place of 1,2-dihydro-6-[p-(4-methyl-1-piperazinyl)-phenyl]-2-oxonicotinic acid any one of the following compounds:

6-[p-(4-Ethyl-1-piperazinyl)phenyl]-1,2-dihydro-2-oxonicotinic Acid.

6-[p-[4-(m-Chlorophenyl)-1-piperazinyl]phenyl]-1,2-dihydro-2-oxonicotinic Acid.

6-[p-(4-Phenyl-1-piperazinyl)phenyl]-1,2-dihydro-2-oxonicotinic Acid.

6-[p-[4-(1-Pyrrolidinyl)piperidino]phenyl]-1,2-dihydro-2-oxonicotinic Acid.

6-[p-(Hexahydro-4-methyl-1H-1,4-diazepin-1-yl)phenyl]-1,2-dihydro-2-oxonicotinic Acid.

6-[p-(4-Methyl-1-piperazinyl)phenyl]-1,2-dihydro-1-methyl-2-oxonicotinic Acid.

6-[o-(4Methyl-1-piperazinyl)phenyl]-1,2-dihydro-2-oxonicotinic Acid.

6-[p-(Dimethylamino)phenyl]-1,2-dihydro-2-oxonicotinic Acid.

6-[m-(Dimethylamino)phenyl]-1,2-dihydro-2-oxonicotinic Acid.

6-[p-(4-Propyl-1-piperazinyl)phenyl]-1,2-dihydro-2-oxonicotinic Acid.

6-(p-Piperidinophenyl)-1,2-dihydro-2-oxonicotinic Acid.

6-(p-Morpholinophenyl)-1,2-dihydro-2-oxonicotinic Acid.

6-[p-(4-Piperidinopiperidino)phenyl]-1,2-dihydro-2-oxonicotinic Acid.

6-[p-(4-Cyclohexyl-1-piperazinyl)phenyl]-1,2-dihydro-2-oxonicotinic Acid.

6-[p-(4-Benzyl-1-piperazinyl)phenyl]-1,2-dihydro-2-oxonicotinic Acid.

one obtains the corresponding acid chloride hydrochloride.

I claim:

1. A process for the production of a 6-(disubstituted amino)phenyl-1,2-dihydro-2-oxonicotinyl chloride hydrochloride having the formula

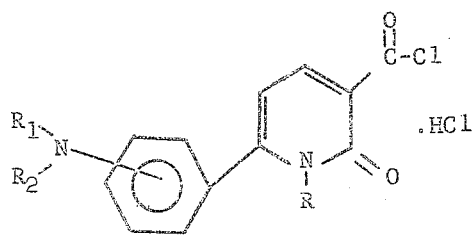

which comprises reacting a compound of the formula

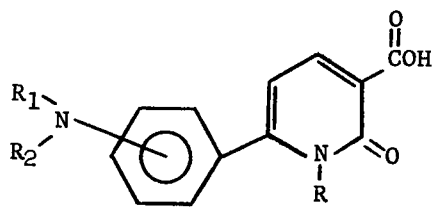

or an acid addition salt thereof having a particle size of less than eight microns, wherein R is hydrogen or methyl; $R_1$ and $R_2$ are branched or straight chain lower alkyl groups of from one to six carbon atoms, or $R_1R_2N$ taken together form 4-$R_3$-1-piperazino, 4-methyl-1-homopiperazino, 1-pyrrolidino, morpholino, 1-piperidino, 4-(1-pyrrolidino)piperidino or 4-(1-piperidino)piperidino, wherein $R_3$ is a lower alkyl group of from one to six carbon atoms, cyclohexyl, benzyl, phenyl, halophenyl wherein halo represents chloro, fluoro, bromo, or iodo, with thionyl chloride at a pressure of about 0.1 to about 0.5 atmospheres and wherein said thionyl chloride is in the gaseous phase.

2. The process of claim 1 wherein R is hydrogen and $R_1R_2N$ taken together form 4-$R_3$-1-piperazino and $R_3$ is a straight or branched lower alkyl group of from one to six carbon atoms or benzyl.

3. The process of claim 1 wherein R is hydrogen and $R_1R_2N$ taken together forms 4-$R_3$-1-piperazino and $R_3$ is a straight or branched lower alkyl group of from one to six carbon atoms or benzyl.

4. The process of claim 1 wherein R is hydrogen and $R_1R_2N$ taken together forms 4-methyl-1-piperazinyl and the $R_1R_2N$ group is in the para position.

* * * * *